United States Patent [19]

Huth et al.

[11] Patent Number: 4,731,358
[45] Date of Patent: Mar. 15, 1988

[54] β-CARBOLINES AND THEIR USE AS TRANQUILIZERS

[75] Inventors: Andreas Huth; Dieter Rahtz; Dieter Seidelmann; Helmut Schmiechen; Helmut Biere, all of Berlin, Fed. Rep. of Germany; Claus T. Braestrup, Roskilde, Denmark

[73] Assignee: Schering Aktiengesellschaft, Berlin and Bergkamen, Fed. Rep. of Germany

[21] Appl. No.: 902,855

[22] Filed: Sep. 2, 1986

Related U.S. Application Data

[63] Continuation of Ser. No. 546,357, Oct. 28, 1983, Pat. No. 4,435,403.

[30] Foreign Application Priority Data

Oct. 29, 1982 [DE] Fed. Rep. of Germany ....... 3240514

[51] Int. Cl.$^4$ ...................... A61K 31/395; C07F 9/32; C07D 471/04
[52] U.S. Cl. ..................... 514/81; 514/292; 546/21; 546/85; 546/86; 546/87
[58] Field of Search ............. 546/85, 86, 87, 21; 514/81, 292

[56] References Cited

U.S. PATENT DOCUMENTS 4,371,536  2/1983  Braestrup et al. ................... 546/85

OTHER PUBLICATIONS

STN International Registry File Search Results P342623z, pp. 228, 229, 231, 244, 274, 227, 225, 214, 211–213, 201, 173, 156, 68, 16, 4, 32, 110, 109, 108, 74, 63, 34, 288, 285, 287, 282, 283, 54, 226, 285, 284, 278, 257, 209, 208, 206, 203, 177, 172, 164, 163, 157, 56, 10, 12, 40, 39, 35, 65, 24, 6, 111, 61, 141, 154.
Goodman et al., The Pharmacological Basis of Therapeutics, p. 28.
Terzyan et al., Izv. Akad. Nauk. Arm. SSR, Nauki 16, No. 1, 87–92 (1963).
Frahn, J. L. Aust. J. Chem. 1974, 27(6), 1367–9 (Eng.).
Ho, Beng-Thong et al., J. Pharm. Sci., 1970, 59(10), 1445–8 (Eng.).
Saxena, J. P. Indian J. Chem. 4(3), 148 (1966) (Eng.).

Primary Examiner—Henry R. Jiles
Assistant Examiner—J. Richter
Attorney, Agent, or Firm—Millen & White

[57] ABSTRACT

New substituted β-carbolines of formula I

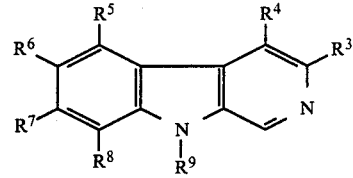

wherein
R$^3$ is hydrogen or a non-carboxyl based substituent, and R$^{4-9}$ have various meanings,
are valuable pharmaceutical products with long lasting action on the central nervous system.

23 Claims, No Drawings

β-CARBOLINES AND THEIR USE AS TRANQUILIZERS

This is a continuation of application Ser. No. 546,357 filed Oct. 28, 1983, now U.S. Pat. No. 4,435,403.

CROSS REFERENCE TO RELATED APPLICATIONS

This application is related to U.S. Pat. No. 4,371,536 and U.S. Ser. No. 331,740 filed on Dec. 17, 1981, now U.S. Pat. No. 4,435,403, whose entire disclosures are incorporated by reference herein.

BACKGROUND OF THE INVENTION

The present invention relates to β-carbolines which have a substituent in the 3-position that is not derived from a carboxylic acid, or which are unsubstituted in the 3-position.

Up to now it has been assumed that the presence of a 3-carboxylic acid or a derivative of a 3-carboxylic acid was necessary for the pharmacological effect of the β-carbolines.

SUMMARY OF THE INVENTION

It is an object of this invention to provide new β-carbolines having pharmacological properties at least as good as those of the prior art but of significantly different structure.

Upon further study of the specification and appended claims, further objects and advantages of this invention will become apparent to those skilled in the art.

These objects have been attained by providing β-carbolines of formula (I):

1. A β-carboline of the formula

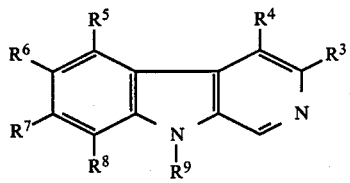

wherein $R^3$ is H; halogen; or $OR^i$ wherein $R^i$ is H, $C_{1-5}$ alkyl, cycloalkyl, aralkyl, aryl or a heterocyclic radical; $NR^{II}R^{III}$, wherein $R^{ii}$ is H, $C_{1-5}$ alkyl, cycloalkyl, aralkyl or aryl, and $R^{III}$ is $C_{1-5}$ alkyl, $C_{1-3}$ acyl, $C_{1-6}$ alkoxycarbonyl, carbamoyl, or $R^{II}$ and $R^{III}$ together with the connecting N atom form a saturated or unsaturated 5- or 6-membered ring; $SO_nR^i$ wherein n is a number of 0 to 2 and $R^I$ is as defined above;

$PO_3R^{IV}R^V$ wherein $R^{IV}$ and $R^V$ are H, $C_{1-5}$ alkyl, cycloalkyl, aralkyl or aryl, wherein $R^{IV}$ and $R^V$ can be the same or different, $C_{1-5}$ alkyl, cycloalkyl, aralkyl, aralkenyl or aryl, wherein the alkyl radical can be substituted by 1 to 3 of halogen, $OR^I$, $NR^{II}R^{III}$, $SO_nR^i$, $COOR^{II}$-$R^{III}$, $CSNR^{II}R^{III}$, $PO_3R^{IV}R^V$, $COR^I$ or CN wherein $R^I$, $R^{II}$, $R^{III}$, $R^{IV}$, $R^V$ and n are as defined above;

$R^4$ is H, $C_{1-5}$ alkyl, alkoxyalkyl, $COR^{VI}$ wherein $R^{VI}$ is H, $C_{1-5}$ alkyl, cycloalkyl, aralkyl, OH, O-alkyl, O-cycloalkyl, O-aralkyl, $NR^{II}R^{II}$, wherein each $R^{II}$ is as defined above and both can be the same or different from one another or with the connecting N atom can form a 5- or 6-membered ring, or $CSR^{VII}$ wherein $R^{VII}$ is H, $C_{1-5}$ alkyl, cycloalkyl or aralkyl, $R^5$-$R^8$ each independently is H, halogen, $NO_2$, $OR^I$, $NR^{II}R^{III}$, $PO_3R^{IV}R^V$, $SO_2NR^IR^V$, $COOR^I$, $CONR^{II}R^{III}$, $CSNR^{II}R^{III}$ or $COR^I$, wherein $R^{I-V}$ are as defined above, and $R^9$ is H, $C_{1-5}$ alkyl, $C_{1-3}$ acyl, carbamoyl, $C_{1-6}$ alkoxycarbonyl or $SO_2R^{VIII}$ wherein $r^{VII}$ is methyl or p-tolyl.

DETAILED DISCUSSION

It has now been found that the new β-carbolines of formula I have the same favorable effects on the central nervous system as known carbolines substituted in the 3-position by a radical containing carboxyl or derived from carboxyl, e.g., as described in the documents incorporated above; however, the new β-carbolines have the advantage that their effect is longer lasting.

The substituents in formula I have various meanings as described. The following discussion applies to all substituents regardless of position unless indicated otherwise.

Unless stated otherwise, halogen according to this invention is fluorine, chlorine, bromine and iodine.

Alkyl by itself or in combination with other atoms or functional groups, e.g., O, S, N, CON, CSN or $PO_3$ includes straight chain or branched groups of up to 5 carbon atoms in each instance, e.g., methyl ethyl, n-propyl, isopropyl, n-butyl, n-pentyl, isobutyl, isopentyl, t-butyl, t-pentyl, etc.

Cycloalkyl includes groups of 3-7 carbon atoms, e.g., cyclopropyl, cyclobutyl, cyclopentyl, cyclohexyl, cycloheptyl etc; suitable aryl groups include those of 6-10 carbon atoms, e.g., phenyl, 1- or 2-naphthyl, etc; suitable aralkyl groups are of 7-10 carbon atoms and include, e.g., benzyl etc.

Suitable heterocyclic radicals include aromatic or non-aromatic, saturated or unsaturated hetero monocycles or bicycles of 5-8 total atoms in each ring and 1-3 hetero atoms (e.g., O, N or S) in each ring, the rest being C-atoms, e.g., pyrrolyl, pyrrolidinyl, piperidinyl, hexamethylenimino, heptamethylenimino, morpholyl, thiomorpholyl, piperazinyl, tetrazolyl, 1,2,3-triazolyl, 1,2,4-triazolyl, imidazolyl, imidazolidinyl, pyrazolyl, pyrazolidinyl, isoxazolyl, oxazolyl, oxazolidinyl, thiazolyl, thiazolidinyl, 1,2,4-oxadiazolyl, 1,2,4-oxadiazolidinyl, and 1,3,4-oxadiazolyl.

Suitable aralkenyl groups are of 8-12 carbon atoms and include, e.g., styryl, etc.

Suitable $C_{1-3}$-acyl groups are derived from aliphatic carboxylic acids, generally alkane carboxylic acids, i.e., alkanoyl.

When $R^{II}$ and $R^{III}$ or $R^{II}$ and $R^{II}$ form a ring with the connecting N-atom which can be saturated, unsaturated or aromatic, they, thus, can be alkylene of 4 or 5 C-atoms, including oxa and/or —N-atoms in the 5 or 6-membered ring.

The aromatic ring can be mono- or disubstituted in positions 5, 6, 7 and/or 8, wherein substitution in the 5- and/or 6-position is preferred.

The new compounds of formula I have valuable pharmacological properties. They are especially effective on the central nervous system and thus are suitable for use as psychopharmacological agents in human or veterinary medicine, i.e., as psychotropic agents. This is demonstrable by fully conventional protocols.

The compounds according to this invention can be used to formulate pharmaceutical preparations, for example for oral or parenteral use in mammals, including man, according to known methods of galenic medicine.

As adjuvants for the formulation of pharmaceutical preparations, the usual physiologically compatible organic and inorganic carriers are suitable for enteral and parenteral use which are inert toward the compounds of this invention.

Examples of suitable carriers include water, salt solutions, alcohols, polyethyleneglycols, polyhydroxyethoxylated castor oils, gelatins, lactose, amylose magnesium stearate, talc, silicic acid, fatty acid mono- and diglycerides, pentaerythritol fatty acid esters, hydroxymethylcellulose, polyvinyl pyrrolidone and the like.

The pharmaceutical preparations can be sterilized and/or combined with adjuvants, such as lubricants, preservatives, stabilizers, wetting agents, emulsifiers, buffers and dyes.

For parenteral use, especially suitable are injectable solutions or suspensions, particularly aqueous solutions of the active compounds in polyhydroxyethoxylated castor oil.

For oral use, especially suitable are tablets, coated tablets or capsules with a talc and/or a hydrocarbon support or binder, such as lactose and corn or potato starch. Administration can also be achieved in liquid form, for example, as a juice to which a sweetener has optionally been added.

The compounds according to this invention are usually formulated into a physiologically compatible carrier in a unit dosage of 0.05-10 mg of active ingredient. The compounds of this invention are usually employed in a dose of 0.1-300 mg per day, preferably 1-30 mg per day for each of the indications mentioned herein. In general, their administration is analogous to that of the well known tranquilizers, e.g., Librium and Stesloid taking into account the usual factors such as differential potencies.

It is known that certain points in the central nervous system of vertebrates have a high specific affinity for bonding to 1,4- and 1,5-benzodiazepines (Squires, R. F. and Braestrup, C., Nature (London) 266 (1977), 734). These locations are called benzodiazepine receptors. The pharmacological properties of the compounds according to the invention were determined by determination of their ability to displace radioactively tagged flunitrazepam from these benzodiazepine receptors.

The displacement activity of the compounds of this invention was determined by measurement of the $IC_{50}$ and $ED_{50}$ values. The $IC_{50}$ value indicates the concentration at which a 50% displacement of the specific binding of $^3H$ flunitrazepam (1.0 nM, 0° C.) is achieved in samples with a total volume of 0.55 ml of a brain membrane suspension, for example of rats.

The displacement test is carried out as follows:

0.5 ml of a suspension of an untreated rat forebrain in 25 mM $KH_2PO_4$ at a pH=7.1 (5-10 mg of tissue per test) is incubated for 40-60 minutes at 0° C. together with $^3H$-diazepam (specific activity 14.4 Ci/mmol, 1.9 nM) or $^3H$ flunitrazepam (specific activity 87 Ci/mmol, 1.0 nM). After incubation, the suspension is filtered through a glass frit, the residue is washed twice with cold buffer solution and the radioactivity is measured on a scintillation counter.

The test is then repeated, except that before the addition of the radioactively tagged benzodiazepine, a predetermined quantity or an excess quantity of the compound, whose displacement activity is to be determined, is added. The $IC_{50}$ value can then be calculated on the basis of the values obtained.

The $ED_{50}$ value is the dose of the test substance that causes a reduction of the specific binding of the flunitrazepam to the benzodiazepine receptor in a living brain to 50% of the control value. Such an in vivo test is performed as follows.

The test substance is normally injected subcutaneously to a group of mice in various doses. After 15 minutes, the $^3H$-flunitrazepam is administered to the mice intravenously. After another 20 minutes, the mice are killed, their frontal meninges are removed and the radioactivity of the frontal meninges is measured by scintillation counting. The $ED_{50}$ value is determined from the dose/effect curves.

The compounds according to this invention exhibit an anti-aggressive effect on mice. The inhibition of aggression was determined on male mice (NMR of Mollegaard, DK) weighing 20-22 g. The mice are kept isolated in plastic cages for three weeks and then, when two mice are placed in the same cage, they spontaneously and almost immediately start fighting with one another. This aggression is effectively inhibited with a series of psychopharmacologically effective substances, including benzodiazepines (Valcelli, Mod. Probl. Pharmacopsych., 1979, 14, 143-156).

The compounds of this invention completely inhibit aggression in a test described by Buus Lasse, Europ. J. Pharmacol., 1978, 47, 45-49. In this test, the compounds of this invention were administered subcutaneously and orally and the anti-aggressive effect was determined after half an hour.

The results of such tests show that the compounds of this invention effectively inhibit aggression and effectively displace flunitrazepam from benzodiazepine receptors. They are, thus, very useful as tranquilizers, non-sedating anticonvulsants, antiaggressives and anxiolytics or for stress protection. As such, they can be used for treatment of the following illustrative indications: anxiety and tension conditions, with and without depressions; unrest; disturbances resulting from stress situations or an excess of stimulation, as well as pathological aggressiveness.

The compounds according to this invention can be produced according to fully conventional methods.

These include processes for producing the compounds of formula I, wherein (a) a 3-hydroxyalkyl compound of formula II

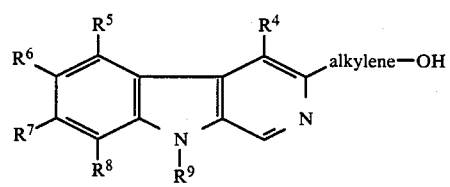

wherein $R^4$, $R^5$, $R^6$, $R^7$, $R^8$ and $R^9$ are as defined in formula I, is conventionally etherified, reduced, halogenated or reacted with an isocyanate of the formula $O=C=N=R^V$ and, optionally, is sulfonated or alkylated in the 9-position;

(b) a compound of general formula III

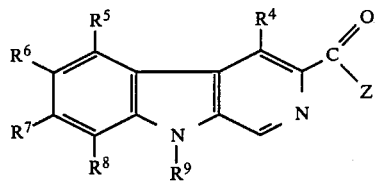

wherein

Z is H or alkoxy of up to 3 C atoms and $R^4$, $R^5$, $R^6$, $R^7$, $R^8$ and $R^9$ are as defined for formula I, is conventionally reacted with a compound of the formula $R^I$MgHal, wherein $R^I$ is as defined above and Hal is Cl, Br or I, and optionally is then reacted with thionyl chloride;

(c) a compound of formula IV

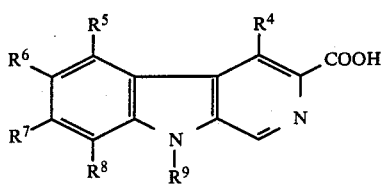

wherein $R^4$, $R^5$, $R^6$, $R^7$, $R^8$, or $R^9$ are as defined in formula I, is conventionally decarboxylated or reacted to form a 3-carboxylic acid azide and the carboxylic acid azide is thermally decomposed in the presence of an alcohol of the formula $R^I$OH according to a Curtius rearrangement;

(d) a 3-haloalkyl-β-carboline of formula V obtained by halogenation according to (a)

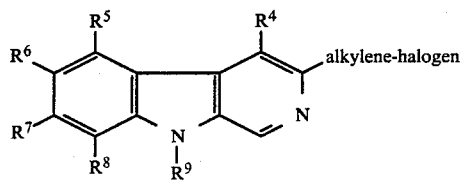

wherein $R^4$, $R^5$, $R^6$, $R^7$, $R^8$ and $R^9$ are as defined in formula I, is conventionally reacted with a Wittig reagent of the formula $Ph_3P=CH=Ph$ or a trialkylphosphite, or an amine of the formula $HNR^{II}R^{III}$ wherein $R^{II}$ and $R^{III}$ are as defined in formula I, or an alcoholate of the formula $MOR^I$, or an alkali mercaptide of the formula $MSR^I$ wherein M is an alkali metal and $R^I$ is as defined in formula I, and to obtain the compounds of formula I wherein $R^3$ is alkylene $SOR^I$ or alkylene $SO_2R^I$, the 3-alkylene-$SR^I$ compounds obtained by reaction with alkali mercaptide are oxidized and optionally halogenated in the 6-position and optionally the halogenated product thus obtained is reacted to form the 6-$COOR^I$ compound and optionally the 6-$COOR^I$ compound is transesterified, saponified or amidated;

(e) a 3-amino-β-carboline of formula VI obtained according to (c) from the 3-carboxylic acid azide by Curtius rearrangement (f) a 1,2,3,4-tetrahydro-β-carboline of formula VII

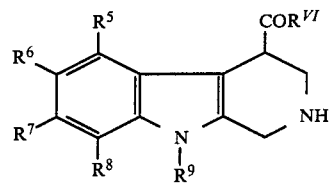

wherein $R^4$, $R^5$, $R^6$, $R^7$, $R^8$ and $R^9$ are as defined above, is conventionally acylated, is reacted with 2,5-dimethoxy-tetrahydrofuran, 1,4-dibromobutane or 1,5-dibromopentane or is reacted in a Sandmeyer reaction with dilute sulfuric acid, with hydrogen halide in the presence of copper(I) halide, with alkali metal cyanide, with $R^I$OH or with $(R^I)_2S$, wherein $R^I$ is as defined above, and, if desired, a 3-$SR^I$ compound obtained from reaction with $(R^I)_2S$ is oxidized to the corresponding 3-$SOR^I$ or 3-$SO_2R^I$ compound and, if desired, the 3-$SR^I$ or 3-$SOR^I$ group is eliminated with Raney nickel/hydrogen and optionally then halogenated in the 6-position and the halogenated product thus obtained is reacted to form the 6-$OR^I$ or 6-$COOR^I$ compound and optionally the 6-$COOR^I$ compound is transesterified, saponified or amidated or nitrated in the 6-position and optionally the resulting nitro compound is reduced to the corresponding amino compound and optionally the amino compound is reacted with alkyl or allyl halide or sulfonated in the 6-position and optionally the chlorosulfonyl compound thus obtained is reacted with an amine;

(f) a 1,2,3,4-tetrahydro-β-carboline of formula VII

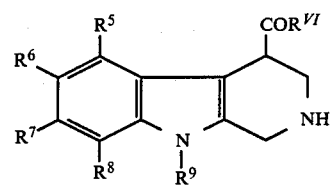

wherein $R^{VI}$, $R^5$, $R^6$, $R^7$, $R^8$ and $R^9$ are as defined for formula I, is conventionally dehydrogenated and, if desired, transesterified in the 4-position, nitrated in the 6- and 8-position, and optionally the resulting nitro compound is reduced to the amino compound and reacted with alkyl or allyl halide or the 4-carboxylic acid is reacted with methyllithium to form the 4-acetyl compound;

(g) a 1,2,3,4-tetrahydro-β-carboline of the formula VIII

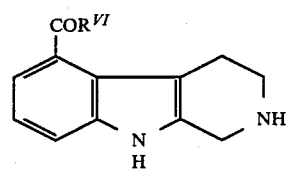

wherein $R^{VI}$ is as defined above, is conventionally dehydrogenated and, if desired, transesterified in the 5-position or the 5-carboxylic acid nitrile is produced from the 5-carboxylic acid through the amide with hexamethylphosphoric triamide;

(h) a 1,2,3,4-tetrahydro-β-carboline of formula IX

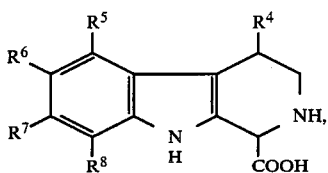

wherein
R⁴, R⁵, R⁶, R⁷ and R⁸ are as defined above, is heated with noble metal catalysts in an inert solvent to 120°–180° C.;

(i) an indole of formula X

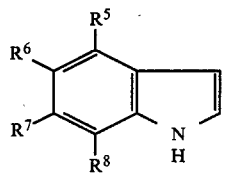

wherein
R⁵, R⁶, R⁷ and R⁸ are as defined above, is reacted with an azadiene of formula XI

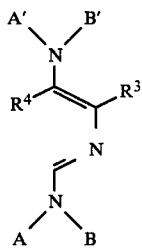

wherein
R³ and R⁴ are as defined above and A and B and also A' and B' each independently, by themselves, are alkyl with 1–3 C atoms or together with the connecting N-atom, form pyrrolidino, piperidino, morpholino or piperazino, in the presence of acids at temperatures of 50°–200° C. and optionally a resulting phosphonic acid monoester in the 3-position is converted to the phosphonic acid diester or a phosphonic acid diester is reacted with a dialkylamine in the presence of oxalyl chloride to form the phosphonic acid-monoester-dialkylamide.

The etherification of the 3-hydroxyalkyl group according to process (a) can be performed in the presence of a strong base with the corresponding $R^I$-halide, wherein $R^I$ is as defined in formula I. To produce alkyl ethers whose carbon chain is broken by an oxygen atom, and optionally is cyclized, the 3-hydroxyalkyl compound of formula II is converted into the appropriate tetrahydropyranyl or alkoxyethyl ether with dihydropyran or alkylvinyl ethers in the presence of a strong acid, such as p-toluenesulfonic acid or phosphorus oxychloride.

The reaction is preferably carried out in the presence of an inert solvent, for example N-methyl-pyrrolidone at temperatures of 0° to 150° C. The hydroxyalkyl group can be reduced to the alkyl groups with zinc powder and glacial acetic acid by trimethylsilyl ether.

The 3-hydroxyalkyl group can be halogenated in the usual manner with a halogenation agent. For example, the 3-hydroxyalkyl group is chlorinated by thionyl chloride into a 3-chloralkyl group.

The 3-hydroxyalkyl group is converted into the N-$R^I$-carbamic acid-3-alkyl ester group with isocyanates of the formula $O=C=N-R^I$, wherein $R^I$ is as defined in formula I.

In addition, a tosyl group can be introduced in the 9-position of the β-carboline with p-toluenesulfochloride in a basic medium, or an alkyl group introduced with N,N-dialkylformamide-dialkylacetal in the presence of a strong base. The following are examples of strong bases: diazabicyclooctane, diazabicyclononene, diazabicycloundecene, but also ethyldiisopropylamine, potassium-tert-butylate, potassium carbonate and powdered potassium hydroxide. For example, pyridine, 4-dimethylaminopyridine, triethylamine and mixtures of these bases serve to form the basic medium.

The Grignard reaction and optionally a subsequent reaction with thionyl chloride of compounds of general formula III according to process (b) occur in the usual manner. Decarboxylation of the 3-carboxylic acids of formula IV preferably takes place in a high-boiling organic base in the presence of copper powder at temperature of 150° to 250° C.

To decompose the carboxyl group and simultaneously introduce a 3-alkoxycarbonyl amino group (urethane group) according to process (c), the 3-carboxylic acid is first converted in known manner into the 3-carboxylic acid azide. This is accomplished preferably by reacting the carboxylic acid with diphenylphosphoryl azide. The carboxylic acid azide is then subjected to Curtius rearrangement (Organic Reactions III (1946)337), whereby the desired urethanes are obtained in the presence of alcohols.

Conversion of the 3-carboxylic acids into 3-alkoxycarbonylamino compounds can also be performed as a stew process without isolating the acid azide. According to a preferred embodiment, a β-carboline-3-carboxylic acid dissolved in dimethyl sulfoxide is added to a solution of diphenylphosphorylazide in alcohol while triethylamine is added and refluxed.

According to process (d), 3-halogenalkyl compounds of formula V obtained from 3-hydroxyalkyl by halogenation are reacted with the Wittig reagent of the formula $Ph_3P=CH-Ph$ to produce corresponding 3-styryl compounds and a trialkylphosphite to produce corresponding 3-styryl kylphosphonoalkyl compounds. Moreover, the corresponding 3-halogenalkyl compounds of formula V are reacted to produce 3-alkylene-$NR^{II}R^{III}$ compounds with an amine of formula $HNR^{II}R^{III}$, in which $R^{II}$ and $R^{III}$ have the meaning indicated in formula I and to produce 3-alkylene $-SR^I$ -or $OR^I$ compounds, with an alkali mercaptide of the formula $MSR^I$ or an alkali alcoholate of the formula $MOR^I$, where M represents an alkali metal and $R^I$ has the meaning indicated in formula I. In each case, the reactions are carried out in an inert solvent at boiling heat. The Wittig reaction is preferably carried out in dimethylformamide or dimethyl sulfoxide, the reaction with trialkylphosphite in excess trialkylphosphite, the amination in alcohol preferably ethanol or propanol, and the reaction with alkali mercaptide or alcoholate preferably in N-methylpyrrolidone, tetrahydrofuran or dioxane.

Oxidation of the thio compounds (3-alkylene-$SR^I$ to 3-alkylene-$SOR^I$ or 3-alkylene $SO_2R^I$ or 3—$SR^I$ to 3—$SOR^I$ or 3—$SO_2R^I$) obtained according to process variant (d) or (e) takes place in a known manner. Suitable oxidizing agents include, for example, organic peroxy acids such as performic acid, peracetic acid, perbenzoic acid, m-chloroperbenzoic acid, monoperphthalic acid, or inorganic peroxides, such as hydrogen peroxide dissolved in water or in diluted organic acids, inorganic oxidizers such as chromic acid, nitric acid, chlorine, bromine, halogen oxyacids, such as hypochlorous, chlorous, choric or iodic acid, tert-butylhypochlorite, organic N-halogen compounds such as N-chlorosuccinimide and N-bromosuccinimide. By choice of the reaction conditions known from the literature, the oxidation potential can be correspondingly adjusted and the reaction to produce the sulfoxides or sulfones can be controlled.

According to process varient (e), the 3-amino compounds of formula VI obtained by the Curtius rearrangement of 3-carboxylic acid compounds via 3-carboxylic acid azide in the 3-position, for example, are acylated or reacted with 2,5-dimethoxy-tetrahydrofuran, 1,4-dibromobutane or 1,5-dibromopentane.

The conversion of the 3-amino compounds into the corresponding 3-hydroxy,3-halogen, 3-cyano, 3—$OR^I$ and 3—$SR^I$ compounds is also performed by known methods, for example, by the Sandmeyer reaction, in which the diazotized product is directly reacted with dilute sulfuric acid, hydrohalic acid in the presence of copper (I) halide, an alkali metal cyanide, $R^IOH$ or $(R^I)_2S$ at elevated temperatures. 3—$SR^I$ compounds can then be oxidized to 3—$SOR^I$ and 3—$SO_2R^I$ compounds.

The compounds obtained according to (d) or (e) then can be halogenated, nitrated or sulfonated for example in the 6-position. Compounds halogenated in the 6-position then can optionally be alkoxylated, thioalkylated, carboxylated or reacted with an amine, all conventionally.

Halogenation in the 6-position takes place according to known methods. For this purpose, the starting material is dissolved in an inert solvent and reacted with the corresponding halogen, such as chlorine or bromine optionally in the presence of a basic catalyst at temperatues below room temperature. Inert solvents include, for example, chlorinated hydrocarbons such as methylene chloride, chloroform, dichloroethylene, etc. Pyridine and substituted pyridine, such as 4-dimethylaminopyridine, are suitable as basic catalysts. A basic catalyst is unnecessary for chlorination.

To feed in iodine, it is advisable not merely to use elementary iodine but a mixture of iodine and iodic acid, whereby the reaction is preferably performed in glacial acetic acid at 80° C. under protonic catalysis. The optional subsequent alkoxylation and thioalkylation of the halogen compounds also take place according to known methods.

The 6-halogen compound, especially the 6-iodine compound, can be carbonylated, for example, with palladium (II) acetate and carbon monoxide in benzyl alcohol and in the presence of a tert-amine, for example triethylamine, tributylamine or pyridine. The 6-benzyloxycarbonyl compound thus obtained can then be saponified, transesterified or reacted with an amine; all in a known way.

For transesterification, the available ester is heated for 3-6 hours to temperatures of 60° to 120° C. with an alcohol $R^IOH$ in the presence of catalytic quantities of $R^IONa$ or NaH. The transesterification can optionally also take place with the alcohol $R^IOH$ in the presence of an acid catalyst such as p-toluene sulfonic acid, HCl, or $CuCl_2$.

Nitrated compounds can be reduced to the corresponding amino compounds and the amino compounds, if desired, can be reacted with alkyl and allyl halides.

Nitration also takes place according to known methods. For this purpose, the starting material is reacted with nitric acid at temperatures below room temperature. Concentrated nitric acid refers to the commercial form, which, however, can also be enriched by fuming nitric acid. In the nitration, the acid acts as both reagent and solvent.

The optional subsequent reduction of the resulting nitro compound into the corresponding amino compound also takes place by known methods.

A preferred method is the reduction with hydrogen in the presence of metal catalysts such as Raney nickel, platinum in finely dispersed form or palladium on a suitable support such as carbon or calcium at normal pressure and room temperature. But it is also possible to use hydrogen in the nascent state, for example by zinc/hydrochloric acid.

Production of sulfonic acids or sulfonic acid derivatives takes place according to known methods. For this purpose, the starting material is dissolved in an inert solvent such as methylene chloride, chloroform, and chlorosulfonic acid is added with cooling.

To produce the corresponding alkylaminosulfonic acid derivatives, the product first thus-obtained is reacted with an alkylamine.

Dehydrogenation of 1,2,3,4-tetrahydro-$\beta$-carbolines of formulae VII and VIII according to (f) and (g) takes place according to known methods.

In one method, the starting material is dissolved or suspended in an inert solvent. All aprotic solvents with boiling points above 100° C. and which are inert to the starting materials are suitable. Examples include xylene, mesitylene, anisols, toluene, chlorobenzene, and diphenyl ether. Then elementary sulfur is added; the quantity should be approximately one mole equivalent of sulfur per double bond. A small excess is not only harmless but advisable. The reaction mixture is refluxed for several hours, wherein the course of the reaction is observed by thin-layer chromatography.

Another method is dehydrogenation with DDQ (dichlorodicyanobenzoquinone) or chloranil in benzene, toluene, xylene, dioxane, tetrahydrofuran, methylene chloride and dimethylethane at temperatures of 0°–60° C. with reaction times of 0.5–4 hours.

Transesterification in the 4- or 5-position, nitration in the 6- and 8-position and reduction of the nitrated compounds to the corresponding amino compounds and alkylation or allylation of the amino compounds with alkyl or allyl bromide can follow the dehydrogenation. The 4-acetyl compound can be produced from the 4-carboxylic acid with methyllithium and the 5-carboxylic acid nitrile can be produced from the 5-carboxylic acid by the amide with hexamethylphosphoric acid triamide.

A further method (h) is the dehydrogenation of 1,2,3,4-tetrahydro-$\beta$-carbolines of formula IX with noble metal catalysts, such as platinum in finely dispersed form, palladium black or palladium carbon, in inert solvents, such as xylene, mesitylene or cumene at 120°–180° C. and reaction times of approximately 0.5–5 hours.

The reaction of an indole derivative and azadiene according to process variant (i) takes place in the presence of acids at temperatures of 50° and 200° C., preferably 75°–150° C. The reaction is carried out, for example, so that the indole derivative of formula X and the azabutadiene of formula XI are heated in organic acids, for example, formic acid, acetic acid, propionic acid or trifluoroacetic acid or in an inorganic medium, for example, phosphoric acid, polyphosphoric acid or phosphoroxychloride, etc. Inert organic solvents, for example toluene, ethyl acetate, dioxane, dimethyloxyethane, acetonitrile, etc., can also be used as diluents.

Catalytic quantities of inorganic acids such as sulfuric acid, hydrochloric acid, perchloric acid, etc., in inert solvent (as above) can also be used for the reaction.

The reaction is ended after several hours. The course of the reaction can be observed by thin-layer chromatography. Once the starting material is reacted after approximately 3–10 hours, the reaction mixture is then processed in the usual manner.

A phosphonic acid diester produced according to method (i) can, if desired, be reacted with a dialkylamine in the presence of oxalyl chloride to form the phosphonic acid monoester dialkylamide.

The substituted β-carboline-3-carboxylic acid esters required as starting materials can be obtained in a known manner by aromatization of correspondingly substituted tetra- or dihydro-β-carboline-3-carboxylic acid esters which in turn are accessible through Pictet-Spengler or Bischler-Napieralski cyclizations from correspondingly substituted tryptophan esters.

More advantageous is the cyclization of suitable unsaturated tryptophan derivatives, for example of αisocyano-indole-3-acryl esters which directly provide the desired β-carboline-3-carboxylic acid ester in one stage.

However, especially simple is the novel and surprising regiospecific reaction of optionally substituted indoles with 2-azabutadiene-3 derivatives according to process variant (i), which provide high yields of optionally substituted β-carboline-3-derivatives in one stage. This novel process is not restricted to the synthesis of β-carboline-3-carboxylic acid esters but can also be applied to the case of variably substituted 2-azadienes (for example, 3-aryl, 3-sulfamoyl, 3-sulfonyl, 3-dialkoxyphosphonyl) in the 3-position for the one-stage synthesis of the corresponding β-carboline-3-derivatives from indoles.

The various options of basic process (i) are disclosed in detail in FRG Patent Applications Nos. P 3240513.8 and P 3240511.1, both of Oct. 29, 1982 and corresponding respectively to U.S. Ser. Nos. 547,555 and 546,356, filed on Oct. 28, 1983, all of whose disclosures are entirely incorporated by reference herein.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

All of the starting materials needed for the above-described processes are either known or readily preparable using fully conventional methods from known or available compounds. See, e.g., the references mentioned above, among others.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Production of 3-hydroxymethyl-β-carbolines

A. 4.3 g of β-carboline-3-carboxylic acid ethyl ester are added to 900 mg of lithium alanate in portions in 200 ml of tetrahydrofuran at 4° C. under argon. It is then stirred for 30 minutes at room temperature and then for 1.5 hours at 80° C. both temperature. Then 30 ml of a 1N aqueous NaOH solution is added by drop during cooling with ice, suctioned off from the precipitate, the filtrate is somewhat concentrated, and the precipitated crystals are suctioned off. 3.15 g of 3-hydroxymethyl-β-carboline with a 230° C. melting point are obtained.

The β-carboline-3-carboxylic acid ethyl ester can be produced as follows:

a. 2 g of α-isocyano-indolyl-3-ethyl acrylate and 200 mg of 1,4-diazabicyclo [2.2.2] octane are brought to boiling in 200 ml of xylene for 18 hours under nitrogen. After evaporation and crystallization from ethanol or acetonitrile, 1,7 g of β-carboline-3-carboxylic acid ethyl ester with a 239° C. melting point are obtained.

b. 1.2 g of indole and 3.2 g of 3-dimethylamino-2-(dimethylaminomethyleneamino-ethyl acrylate (produced according to W. Kantlehner et al., Liebigs Ann. Chem., 1980, 344) A)) are dissolved in 17 ml of glacial acetic acid under nitrogen and refluxed until not starting indole is any longer visible (6 hours) by thin-layer chromatography. After distilling off of most of the solvent, it is poured in water and the crystallate suctioned off. After recrystallization from acetonitrile, 1.45 g of the title compound with a 234° C. melting point are obtained.

B. Analogously, the following are produced from the corresponding esters:

6-bromo-3-hydroxymethyl-β-carboline, 285°–290° C. melting point;

6-iodo-3-hydroxymethyl-β-carboline;

4-methyl-3-hydroxymethyl-β-carboline, 219°–225° C. melting point (ethyl acetate/ethanol);

4-propyl-3-hydroxymethyl-β-carboline, 180°–182° C. melting point;

6-amino-3-hydroxymethyl-β-carboline, 220° C. melting point;

5-benzyloxy-4-methoxymethyl-3-hydroxymethyl-β-carboline, 188°–190° C. melting point (ethyl acetate/methanol);

6-chloro-3-hydroxymethyl-β-carboline, 285°–297° C. melting point (tetrahydrofuran).

C. Production of 6-acetylamino-3-hydroxymethyl-β-carbolines 106 mg of 6-amino-3-hydroxymethyl-β-carboline are stirred in in 3 ml of glacial acetic acid with 52 mg of acetic anhydride at room temperature for 1.5 hours. After filtering and concentration, recrystallization from ethanol/cyclohexane takes place and 24 mg of 6-acetylamino-3-hydroxymethyl-β-carboline are obtained.

EXAMPLE 1

6-bromo-0-(tetrahydropyran-2-yl)-β-carboline-3-methanol 1.2 g of 6-bromo-3-hydroxymethyl-β-carboline are stirred in 30 ml of N-methylpyrrolidone together with 180 mg of p-toluenesulfonic acid and 30 ml of dihydropyran for 3 hours at 110° C. bath temperature. After evaporation in a bulb tube, the residue is chromatographed on silica gel with chloroform/ethanol=10:2. 700 mg of 6-bromo-0-(tetrahydropyran-2-yl)-β-carboline-3-methanol with a 224°-226° C. melting point are obtained from the corresponding fractions by recrystallization from ethyl acetate.

EXAMPLE 2

6-bromo-9-tosyl-0-(tetrahydropyran-2-yl)-β-carboline-3-methanol 700 mg of 6-bromo-0-(tetrahydropyran-2-yl)-β-carboline-3-methanol together with 0.7 ml triethylamine, 90 mg of dimethylaminopyridine and 400 mg of p-toluenesulfochloride are refluxed in 50 ml of methylenechloride for one hour. It is then washed once with 2N aqueous HCl and twice with water and the organic phase is dried, filtered and concentrated. The residue is recrystallized from ethyl acetate/cyclohexane or from toluene and 900 mg of 6-bromo-9-tosyl-0-(tetrahydropyran-2-yl)-β-carboline-3-methanol with a 212°-215° C. melting point are obtained.

EXAMPLE 3

3-(1-ethyl-1-hydroxypropyl)-β-carboline 480 mg of β-carboline-3-carboxylic acid estyl ester are dissolved in 40 ml of tetrahydrofuran and added drop by drop to a Grignard solution consisting of 144 mg of magnesium chips and 660 mg of ethylbromide in 10 ml of diethyl ether. After 2 hours of reflux it is mixed with aqueous ammonium chloride solution and extracted with methylene chloride. After drying, filtering and evaporation, the residue is chromatographed on silica gel with toluene/glacial acetic acid/water=10:10:1 as eluant. 120 mg of 3-(1-ethyl-1-hydroxy-propyl)-β-carboline are obtained as oil.

EXAMPLE 4

3-(1-hydroxyethyl)-β-carboline

Analogously to example 3,3-(1-hydroxyethyl)-β-carboline with a 172°-174° C. melting point (ethyl acetate/hexane) is produced from 3-formyl-β-carboline.

EXAMPLE 5

3-methyl-β-carboline 2 g of 3-hydroxymethyl-β-carboline, 3.7 g of sodium iodide and 2.5 ml of chlorotrimethylsilane are stirred in 50 ml of N,N-dimethylformamide at a bath temperature of 35° C. for 4 hours. 3 g of zinc powder and 10 ml of glacial acetic acid are added to the resulting yellow suspension and stirred for another 18 hours at 80° C. The reaction mixture is allowed to clarify on Celite and the filtrate is concentrated under vacuum. The resulting oil is chromatographed on silica gel (methylene chloride/ethanol: 9+1). 0.825 g of 3-methyl-β-carboline with a 255°-256° C. melting point was obtained.

EXAMPLE 6

3,9-dimethyl-β-carboline 0.182 g of 3-methyl-β-carboline (example 5), 0.5 ml of N,N-dimethylformamide-dimethylacetal (90%) and 0.02 g of diazabicyclooctane (Dabco) are stirred in 30 ml of absolute N,N-dimethylformamide for 15 hours at 110° C. The solvent is distilled off under vacuum and the residue is chromatographed on silica gel. (Methylene chloride/ethanol: 9+1). 0.095 g of 3,9-dimethyl-β-carboline with a 134° C. melting point (decomposition) is obtained.

EXAMPLE 7

N-phenyl-carbamic acid-(β-carboline-3-yl-methyl)-ester 0.198 g of 3-hydroxymethyl-β-carboline are dissolved in 30 ml of toluene and mixed with 0.1 ml of phenylisocyanate. The solution is stirred for 4 hours at 70° C. bath temperature. After cooling, the precipitate is filtered off, washed with toluene and dried under vacuum. 0.188 g of N-phenyl-carbamic acid-(β-carboline-3-yl-methyl)ester with a 153°-155° C. melting point (decomposition) is obtained.

EXAMPLE 8

N-methyl-carbamic acid-(9-methylcarbamoyl-β-carbolin-3-yl-methyl)-ester 0.238 g of N-methylcarbamic acid-(9-methylcarbamoyl-β-carboline-3-yl-methyl)-ester with a 153°-154° C. melting point (decomposition), as in example 7, is obtained from 0.198 g of 3-hydroxymethyl-β-carboline and 0.22 ml methylisocyanate.

EXAMPLE 9

3-chloromethyl-β-carboline 400 mg of 3-hydroxymethyl-β-carboline are refluxed in 8 ml of thionyl chloride for one hour. After evaporation, 450 mg of 3-chloromethyl-β-carboline are obtained as hydrochloride.

EXAMPLE 10

3-(1-chloroethyl)-β-carboline

Analogously to example 9,3-(1-chlorethyl)-β-carboline with a melting point starting at 225° C. (while decomposing) is produced from 3-(1-hydroxyethyl)-β-carboline.

EXAMPLE 11

3-(1-ethoxyethyl)-β-carboline 200 mg of 3-(1-hydroxyethyl)-β-carboline (example 4) are refluxed in 1 ml of thionyl chloride for 3 hours. After distilling off, it is chromatographed on silica gel with methylene chloride/ethanol=10:1 as eluant. 117 mg of 3-(1-ethoxyethyl)-β-carboline are obtained as oil.

EXAMPLE 12

3-styryl-β-carboline 0.51 g of 3-chloromethyl-β-carboline (example 9) and 0.524 g triphenylphosphine are refluxed in 30 ml of absolute N,N-dimethylformamide for 20 hours. The solvent is distilled off under vacuum, the reaction product is picked up in 30 ml of methanol and mixed with an equivalent amount of benzaldehyde. To this is added drop by drop within 10 minutes a solution of 0.075 g of sodium and 10 ml of absolute methanol and then refluxed for 14 hours. The solvent is drawn off under vacuum and the residue picked up in methylene chloride, filtered on Celite and the filtrate concentrated under vacuum. The resulting reaction mixture is chromatographed on silica gel (methylene chloride/ethanol=9:1). 0.150 g of 3-styryl-$\beta$-carboline with a 204°–207° C. melting point is obtained.

EXAMPLE 13

3-N,N-dimethylaminomethyl-$\beta$-carboline 300 mg of 3-chloromethyl-$\beta$-carboline hydrochloride (example 9) are refluxed in 10 ml of ethanol with 5 ml of diethylamine for one hour. After evaporation it is dispersed in methylene chloridaqueous ammonia. The organic phase is dried, evaporated and recrystallized from acetone. 100 mg of 3-N,N-dimethylaminomethyl-$\beta$-carboline with a 122°–123° C. melting point are obtained.

EXAMPLE 14

3-methylthiomethyl-$\beta$-carboline 126 mg of 3-chloromethyl-$\beta$-carboline hydrochloride (example 9) are added to a suspension of sodium methyl mercaptide prepared from 33 mg of 80% sodium hydride and methyl mercaptan in 10 ml of absolute tetrahydrofuran and refluxed for one hour. After dilution with water, the methylene chloride is extracted. The organic phase is washed with sodium bicarbonate solution, dried, filtered and concentrated. After recrystallization from diisopropyl ether with a little ethyl acetate, 55 mg of 3-methylthiomethyl-$\beta$-carboline with a 156°–157° C. melting point are obtained.

EXAMPLE 15

3-methylsulfinylmethyl-$\beta$-carboline 160 mg of 3-methylthiomethyl-$\beta$-carboline are stirred in 15 ml of methylene chloride with 163 mg of m-chloroperbenzoic acid for 3 hours at room temperature. After extraction with semiconcentrated sodium bicarbonate solution, the organic phase is dried, filtered and concentrated. The residue is stirred with ethyl acetate/ethanol. 76 mg of 3-methylsulfinylmethyl-$\beta$-carboline with a 175°–178° C. melting point are obtained as a residue.

EXAMPLE 16

3-methylsulfonylmethyl-$\beta$-carboline 190 mg of methylthiomethyl-$\beta$-carboline are mixed in 25 ml of methylene chloride with 382 mg of m-chloroperbenzoic acid and refluxed for one hour. After extraction with 30 ml of semiconcentrated sodium bicarbonate solution, the organic phase is dried, filtered and concentrated. After recrystallization from ethanol, 56 mg of 3-methylsulfonylmethyl-$\beta$-carboline with a 218°–220° C. melting point are obtained.

EXAMPLE 17

3-diethylphosphonomethyl-$\beta$-carboline 504 mg of 3-chloromethyl-$\beta$-carboline hydrochloride are stirred with 4 ml of triethylphospite for 2 hours at 120°–130° C. and after cooling, are chromatographed on silica gel with methylene chloride/methanol=10:2. 57 mg of 3-diethylphosphonomethyl-$\beta$-carboline are obtained as oil.

EXAMPLE 18

6-iodine-3-methylsulfinyl-$\beta$-carboline 1.07 g of 3-methylthio-$\beta$-carboline are stirred in 10 ml of glacial acetic acid with 0.24 ml of water, 0.06 ml of concentrated sulfuric acid, 0.172 g of iodic acid and 0.442 g of iodine at 80° C. bath temperature for 4 hours. After addition of 172 mg of iodic acid and 442 mg of iodine, heating at 80° C. is continued for another 3 hours. After suctioning off of the precipitated crystals, 0.7 g of 6-iodo-3-methylsulfinyl-$\beta$-carboline with a 280°–285° C. melting point is obtained.

EXAMPLE 19

6-benzyloxycarbonyl-3-methylsulfinyl-$\beta$-carboline 1.3 g of 6-iodo-3-methylsulfinyl-$\beta$-carboline are carbonylated in 21 ml of benzylalcohol with 0.96 ml of tributylamine and 38 mg of palladium (II) acetate under 1 atmosphere of carbon monoxide for 4 hours at 110° C. After distilling off of the benzyl alcohol, it is picked up in 75 ml of methylene chloride and extracted once with 50 ml of 1N aqueous hydrochloric acid, once with saturated bicarbonate solution and once with saturated sodium chloride solution. The organic phase is dried, filtered and concentrated and the residue is recrystallized from ethyl acetate/hexane, whereby 630 mg of 6-benzyloxycarbonyl-3-methylsulfonyl-$\beta$-carboline with a 220°–223° C. melting point are obtained.

EXAMPLE 20

6-ethoxycarbonyl-3-methylsulfinyl-$\beta$-carboline 270 mg of 6-benzyloxycarbonyl-3-methylsulfinyl-$\beta$-carboline are refluxed for 1.5 hours with an alcoholate solution prepared from 27 mg 80% sodium hydride and 15 ml of absolute ethanol. After concentration, it is picked up in ethyl acetate and suctioned off. 78 mg of 6-ethoxycarbonyl-3-methylsulfinyl-$\beta$-carboline with a 240°–243° C. melting point are obtained.

EXAMPLE 21

6-ethoxycarbonyl-$\beta$-carboline 150 mg of 6-carboxyethyl-3-methylsulfinyl-$\beta$-carboline are hydrogenated in 20 ml N-methylpyrrolidinone at 60° C. for 2 hours under a pressure of 50 bar of hydrogen in the presence of 100 mg Raney nickel (type B-113-Z). After suctioning off over a G-4 frit, it is evaporated and the residue boiled with ethyl acetate and 3 drops of ethanol. After suctioning off, 68 mg of 6-ethoxycarbonyl-$\beta$-carboline with a 243°–244° C. melting point are obtained.

EXAMPLE 22

6-dimethylaminocarbonyl-$\beta$-carboline 150 mg of 6-ethoxycarbonyl-$\beta$-carboline are heated in 5 ml of ethylene gylcol with 2 ml of dimethylamine solution for 20 hours to 100° C. After cooling, it is placed on ice, extracted with ethyl acetate and the organic phase is dried, filtered and concentrated. 50 mg of 6-dimethylaminocarbonyl-$\beta$-carboline are obtained as oil after chromatography on silica gel with methylene chloride/ethanol=10:1.

EXAMPLE 23

6-piperidino-4-methyl-β-carboline 2.5 g of 6-piperidino-4-methyl-β-carboline-3-carboxylic acid are heated with 520 mg of copper powder in 50 ml of quinoline for 1.5 hours to 190°–220° C. bath temperature. After distilling off the quinoline in a bulb tube, it is dispersed in ethyl acetate/10% aqueous ammonia. The precipitate that is formed is filtered off and absorptively precipated with ethanol. The combined evaporation residue of the ethanol extraction and the ethyl acetate phase yields 690 mg of 6-piperidino-4-methyl-β-carboline with a 235°–238° C. (decomposition) melting point by crystallization from ethylacetate/diisopropylether.

EXAMPLE 24

6-N,N-dimethylsulfonamido-β-carboline

Analogously, 6-N,N-dimethylsulfonamido-β-carboline is produced from 6-N,N-dimethylsulfonamido-β-carboline-3-carboxylic acid; melting point: 223°–226° C. (ethanol).

EXAMPLE 25

3-tert-butoxycarbonylamino-β-carboline 0.25 g of β-carboline-3-carboxylic acid are dissolved in 4 ml of dimethylsulfoxide while being heated. 10 ml of tert-butanol, 0.25 ml of diphenylphosphoryl azide and 0.17 ml of triethylamine are added to the solution. The reaction mixture is refluxed for 15 minutes. The crystals precipitated during cooling are filtered off, the tert-butanol is evaporated from the filtrate under vacuum and the residue is mixed with 10 ml of water. 0.025 g of 3-tert-butoxycarbonylamino-β-carboline with a 185°–190° C. melting point (methanol) is obtained from the resulting precipitate by chromatography on silica gel (methylene chloride with 5% methanol).

EXAMPLE 26

3-methoxycarbonylamino-β-carboline 4 g of β-carboline-3-carboxylic acid azide are refluxed in 250 ml of methanol for 6 hours. Then the solution is evaporated and the residue is recrystallized twice from ethyl acetate. 0.14 g of 3-methoxycarbonylamino-β-carboline with a 236°–238° C. melting point are obtained.

The β-carboline-3-carboxylic acid azide needed as starting material is produced as follows:

3.4 g of diphenylphosphoryl azide and 2.2 ml of triethylamine are added to the solution of 3.3 g β-carboline-3-carboxylic acid in 85 ml of dimethylsulfoxide. The solution temporarily turns purple and a precipitate results. After the solution is left standing overnight, the precipitate is filtered off and the filtrate is mixed into 0.8 l of water. The precipitate is suctioned off and dried. Melting point: 138° C. (deflagration).

EXAMPLE 27

3-acetamino-β-carboline 2 g of 3-amino-β-carboline are suspended in 35 ml of pyridine and mixed with 4 ml of acetic anhydride. The aminocarboline dissolves during slight heating. After 20 minutes the solution is evaporated. The crystalline residue is washed with water and is recrystallized from ethyl acetate. Yield: 1.5 g of 3-acetamino-β-carboline with a 200°–203° C. melting point.

EXAMPLE 28

3-(I-pyrrolyl)-β-carboline 0.74 g of 3-aminocarboline and 0.54 g of 2,5-dimethoxytetrahydrofuran are heated in 10 ml of glacial acetic acid for 15 minutes in a steam bath. After cooling, the precipitated crystals are suctioned off and are chromatographed on silica gel with a mixture of 10 parts of methylene chloride and one part of ethanol.

Yield: 0.12 g of 3-(I-pyrrolyl)-β-carboline; melting point: 165°–170° C.

EXAMPLE 29

3-piperidino-β-carboline 549 mg of 3-amino-β-carboline are refluxed for 4 hours with 1.5 g of 1,5-dibromopentane and 1 g of diazabicycloundecene in 25 ml of tetrahydrofuran and 5 ml of absolute ethanol. After evaporation, the product is chromatographed on silica gel with cyclohexane/ethyl acetate=1:1 as eluant. 50 mg of 3-piperidino-β-carboline are obtained as oil.

EXAMPLE 30

3-hydroxy-β-carboline 0.75 g of 3-amino-β-carboline are dissolved in 85 ml of 6-molar sulfuric acid and at 0° C. mixed with a solution of 0.435 g of sodium nitrite in 10 ml of water. The reaction mixture is stirred for an hour at 0° C. and then added drop by drop to 320 ml of boiling 2-molar sulfuric acid and then refluxed for another 20 minutes. After standing overnight, the product is neutralized with sodium hydroxide and extracted with a mixture consisting of 10 parts of ethyl acetate and one part of ethanol. The ethyl acetate extract is washed once with water, dried and evaporated. The evaporation residue is recrystallized from dimethylformamide. Thus 0.2 g of 3-hydroxy-β-carboline are obtained

EXAMPLE 31

3-bromo-β-carboline 2 g of 3-amino-β-carboline, suspended in 25 ml of 48% hydrobromic acid, are mixed with 6 ml of a 2-molar sodium nitrite solution at 0°–5° C. The mixture is added at 0°–5° C. to a solution of 2.1 g of copper-I-bromide in 20 ml of 24% hydrobromic acid. The reaction mixture is heated briefly in a steam bath and then repeatedly extracted with a mixture consisting of 9 parts of ethyl acetate and one part of ethane. The combined extracts are evaporated, the residue chromatographed (silica gel, methylene chloride/methanol=19:1). The main fraction crystallizes on treatment with ethyl acetate. Yield: 0.5 g of 3-bromo-β-carboline; melting point: 300° C.

EXAMPLE 32

The 3-chloro-β-carboline is produced analogously to Example 31. Melting point: 307°–308° C.

EXAMPLE 33

3-ethoxy-β-carboline 1 ml of isoamylnitrite is added to a suspension of 1 g of 3-amino-β-carboline in 100 ml of ethanol and 2 ml of concentrated sulfuric acid. The mixture is stirred at room temperature for an hour and then refluxed for an hour. As a result, a clear solution is obtained. After cooling, it is poured into a mixture of 100 ml of water and 100 ml of saturated sodium bicarbonate solution. It is extracted three times with 100 ml of ether each time and the evaporation residue of the combined ether extracts is chromatographed (silica gel, methanol/chloroform=95:5) and recrystallized from hexane. Yield: 0.3 g of 3-ethoxy-β-carboline with a melting point of 130°-133° C.

EXAMPLE 34

The 3-methoxy-β-carboline with a 184°-189° C. melting point is produced analogously to Example 33.

EXAMPLE 35

3-propoxy-β-carboline 184 mg of 3-amino-β-carboline are mixed with 0.5 ml of i-amylnitrite in 15 ml of n-propanol at room temperature and stirred for 15 minutes. Then it is heated for 4.5 hours to 80° C. bath temperature. After concentration, it is chromatographed on silica gel with methylene/chloride/acetone=1:1 as eluant. After concentration and recrystallization of the corresponding fractions from diisopropyl ether/cyclohexane, 120 mg of 3-propoxy-β-carboline with a 147°-151° C. melting point are obtained.

EXAMPLE 36

The following are produced in accordance with the process indicated in Example 35:
3-isopropoxy-β-carboline (petroleum ether absorptively precipitated)
3-benzyloxy-β-carboline, melting point: 174°-175° C., (diisopropyl ether/cyclohexane);
3-cyclohexyloxy-β-carboline, melting point: 138°-139° C., (diisopropyl ether/cyclohexane);
3-(1-methoxyethoxy)-β-carboline, melting point: 83°-85° C., (diisopropyl ether/cyclohexane);
3-t-butoxy-β-carboline, melting point: 208°-212° C., (diisopropyl ether/cyclohexane);
3-butoxy-β-carboline, melting point: 114°-115° C., (cyclohexane);
3-isopentoxy-β-carboline, melting point: 95° C.

EXAMPLE 37

3-ethylthio-β-carboline 732 mg of 3-amino-β-carboline in 7 ml of diethyldisulfide are heated to 80° C. and mixed with 1 ml of isoamylnitrite. After 0.5 hours of heating to 80° C., it is again mixed with 1 ml of isoamylnitrite and heated to 80° C. for 1.5 hours. After distilling off, the residue is chromatographed twice on silica gel with ethyl acetate/cyclohexane as eluant. After absorptive precipitation of the corresponding evaporated fraction with cyclohexane/diisopropyl ether, 206 mg of 3-ethylthio-β-carboline with a 132°-133° C. melting point are obtained.

EXAMPLE 38

The following are produced in a corresponding manner:
4-methyl-3-methylthio-β-carboline with 183°-185° C. melting point (absorptively precipitated diisopropyl ether/cyclohexane);
3-benzylthio-β-carboline with a 150° C. melting point (ethyl acetate/diisopropyl ether);
3-methylthio-β-carboline with a 178°-179° C. melting point, (chromatographically purified).

EXAMPLE 39

6-nitro-3-methylthio-β-carboline 970 mg of 3-methylthio-β-carboline are stirred for 4 hours at room temperature with 60 ml of 65% nitric acid. After introduction of the preparation into water, it is suctioned off and dried. 950 mg of 6-nitro-3-methylthio-β-carboline with a >250° C. melting point are obtained.

EXAMPLE 40

6-amino-3-methylthio-β-carboline 950 mg of 6-nitro-3-methylthio-β-carboline are hydrogenated in 80 ml of tetrahydrofuran and 80ml of ethanol with 200 mg of palladium/carbon (10%) for 7.5 hours at room temperature under normal hydrogen pressure. After filtration and concentration, the residue is chromatographed on silica gel with methylene chloride/acetone=1:1 as eluant. 600 mg of 6-amino-3-methylthio-β-carboline with a 202° C. melting point are obtained.

EXAMPLE 41

6-diallylamino-3-methylthio-β-carboline 229 mg of 6-amino-3-methylthio-β-carboline are heated in 15 ml of ethanol (absolute) with 0.27 ml of allylbromide and 0.37 ml of diazabicycloundecene for 3 hours to 70° C. After concentration to dryness, it is dispersed in ethyl acetate/saturated sodium chloride solution. The organic phase is dried, filtered and concentrated. After trituration of the residue with diisopropyl ether, 70 mg of 6-diallylamino-3-methylthio-β-carboline with a 110° C. melting point are obtained.

EXAMPLE 42

6-diethylamino-β-carboline 150 mg of 6-amino-3-methylthio-β-carboline are refluxed for 2 hours in 5 ml of ethanol with a spatula tip of Raney nickel. 22 mg of 6-diethylamino-β-carboline as oil are obtained after filtering and evaporation.

EXAMPLE 43

6-amino-β-carboline 660 mg of 6-nitro-3-methylthio-β-carboline are hydrogenated in 50 ml of N-methylpyrrolidone with 3 g of Raney nickel at 50 bar of $H_2$ pressure and 60° C. for 2 hours. After filtering, it is evaporated and the residue chromatographed on silica gel with methylene chloride/ethanol=10:2 as eluant. 320 mg of 6-amino-β-carboline as oil are obtained.

EXAMPLE 44

6-diallylamino-β-carboline 360 mg of 6-amino-β-carboline are heated in 20 ml of ethanol with 0.54 ml of allylbromide and 0.74 ml diazabicycloundecene for 3 hours at 70° C. After concentration to dryness and dispersing in ethyl acetate/saturated sodium chloride solution, the organic phase is separated, dried, filtered and concentrated. The residue is chromatographed on silica gel with cyclohexane/ethyl acetate=1:1 as eluant and 50 mg of 6-diallylamino-β-carboline as oil are obtained.

EXAMPLE 45

6-chlorosulfonyl-3-methylthio-β-carboline and 6,8-bis-(chlorosulfonyl)-3-methylthio-β-carboline 400 mg of 3-methylthio-β-carboline are added in portions to 1 ml of chlorosulfonic acid at 0° C. After one hour at room temperature, it is slowly put on ice, suctioned off, and the residue dried and then heated in 5 ml of thionylchloride with 2 drops of dimethylformamide. 500 mg of a mixture of 6-chlorosulfonyl-3-methylthio-β-carboline and 6,8-bis-(chlorosulfonyl)-3-methylthio-β-carboline are obtained after concentration.

EXAMPLE 46

6-dimethylaminosulfonyl-3-methylthio-β-carboline and 6,8-bis-(dimethylaminosulfonyl)-3-methylthio-β-carboline 200 mg of the mixture obtained according to example 45 are mixed with 10 ml of an ice cold 40% dimethylamine solution and heated for 5 minutes to 100° C. After cooling, it is diluted with water and extracted with ethyl acetate. After chromatography on silica gel with methylene chloride/ethanol=95:5 as eluant, 130 mg of 6-dimethylaminosulfonyl-3-methylthio-β-carboline with a 298°–300° C. melting point are obtained as well as 90 mg of 6,8-bis-(dimethylaminosulfonyl)-3-methylthio-β-carboline with a 249°–265° C. melting point.

EXAMPLE 47

6-diallylaminosulfonyl-3-methylthio-β-carboline and 6,8-bis-(diallylaminosulfonyl)-3-methylthio-β-carboline The following are produced analogously to example 46: 6-diallylaminosulfonyl-3-methylthio-β-carboline, melting point: 211° C.; and 6,8-bis-(diallylaminosulfonyl)-3-methylthio-β-carboline, melting point: 148° C.

EXAMPLE 48

β-carboline-4-carboxylic acid ethyl ester 0.9 of 1,2,3,4-tetrahydro-β-carboline-4-carboxylic acid ethyl ester hydrochloride is stirred with 0.22 g sulfur powder in 9 ml of dimethylsulfoxide under argon for 1.5 hours at 130° C. From the evaporated reaction mixture, 0.4 g of β-carboline-4-carboxylic acid-ethyl ester hydrochloride with a 238°–240° C. melting point can be extracted with ethanol.

The starting material is produced from the 1,2,3,4-tetrahydro-β-carboline-4-carboxylic acid by esterification with ethanol and thionyl chloride in a known manner.

EXAMPLE 49

β-carboline-4-carboxylic acid propyl ester

The compound is produced by transesterification of the β-carboline-4-carboxylic acid-ethyl ester-hydrochloride with n-propanol.

EXAMPLE 50

6-nitro and 8-nitro-β-carboline-4-carboxylic acid-ethyl ester 1 g β-carboline-4-carboxylic acid-ethyl ester-hydrochloride are introduced into 20 ml of 65% nitric acid at room temperature while stirring. After 15 minutes, it is heated to 75° C. for one hour. After cooling, the reaction mixture is poured into ice water. The precipitate is suctioned off and recrystallized from ethyl acetate.

Yield: 0.56 g of 6-nitro-β-carboline-4-carboxylic acid-ethyl ester nitrate.

Melting point: 218°–220° C.

The 8-nitro-β-carboline-4-carboxylic acid ethyl ester can be isolated from the above-mentioned glacial acetic acid mother liquor or chromatographically, from the not yet recrystallized raw product (silica gel, toluene-glacial acetic acid-water=10:10:1).

EXAMPLE 51

6-amino and 8-amino-β-carboline-4-carboxylic acid ethyl ester 3.3 g of mixture of 6-nitro and 8-nitro-β-carboline-4-carboxylic acid ethyl ester (example 50) are hydrogenated in 400 ml of ethanol and with addition of 20 g of Raney nickel at normal pressure and room temperature. The isomer mixture is separated by chromatography on silica gel (toluene/glacial acetic acid/water=10:10:1). After crystallization from ethyl acetate, 0.5 g of 6-amino-β-carboline-4-carboxylic acid ethyl ester with a >340° C. melting point are isolated as more polar components.

The isomer more nonpolar 8-amino-β-carboline-4-carboxylic acid ethyl ester is obtained in a yield of 0.2 g with a 262°–265° C. melting point by dissolution in hot ethyl acetate, cooling, filtering and evaporation of the mother liquor.

EXAMPLE 52

6-diallylamino-β-carboline-4-carboxylic acid ethyl ester

A solution of 0.28 g of 6-amino-β-carboline-4-carboxylic acid ethyl ester, 0.18 g of diazabicycloundecane and 0.26 g of allylbromide in 5 ml of ethanol is heated for 3 hours to 70° C. Then the solution is evaporated. The evaporation residue is extracted with ethyl acetate and water, the combined extracts are evaporated and chromatographed on silica gel with methylene chloride/methanol=5:1. Yield: 0.05 g.

EXAMPLE 53

4-acetyl-β-carboline

The reaction of β-carboline-4-carboxylic acid with methyllithium analogous to the process described by C. Tegner (Act. Chem. Scand. 6, 782–90) for the reaction of benzoic acid with methyllithium yields 4-acetyl-β-carboline.

The β-carboline-4-carboxylic acid needed as starting material is produced from β-carboline-4-carboxylic acid ethyl ester (example 48) by heating with aqueous alcoholic sodium hydroxide solution.

EXAMPLE 54

β-carboline-5-carboxylic ethyl ester 0.86 g of 5-ethoxycarbonyl-1,2,3,4-tetrahydro-β-carboline-1-carboxylic acid are refluxed for 50 minutes in 200 ml of xylene with 0.65 g of 10% palladium/carbon. The solution is evaporated after filtering off of the catalyst. The residue is boiled first with xylene and then with ethanol. The extracts are mixed, evaporated and chromatographed on silica gel with ethanol/methylene chloride 1:10.

After treatment with ether, 0.48 g β-carboline-5-carboxylic acid ethyl ester with a 195°–201° C. melting point is obtained.

The starting material required for the synthesis is produced as follows:

A. 4-ethoxycarbonyl-3-(2-nitrovinyl)-indole 5 g of 4-ethoxycarbonyl indole are added to a solution of 3.1 g of dimethylamino-2-nitroethylene in 20 ml of trifluoroethyl acetate refrigerated under argon. The reaction mixture is introduced into ice water after it had been standing overnight at room temperature. The aqueous phase is repeatedly extracted with ethyl acetate. The combined ethyl acetate extracts are extracted first with sodium bicarbonate solution, then a saturated sodium chloride solution, dried and evaporated. The residue is recrystallized from ethanol. Yield: 4.5 g of 4-ethoxycarbonyl-3-(2-nitrovinyl)-indole. Yellow crystals with a 197°–199° C. melting point.

B. 3-(2-aminoethyl)-4-ethoxycarbonyl indole 0.5 g of 4-ethoxycarbonyl-3-(2-nitrovinyl)indole are heated under nitrogen for 45 minutes in the steam bath in 50 ml of formic acid with 1.5 g of 10% palladium-carbon. The palladium carbon is then filtered off, the filtrate evaporated, the evaporation residue [3-(2-aminoethyl)-4-ethoxycarbonyl indole] is then further reacted immediately.

C. 5-ethoxycarbonyl-1,2,3,4-tetrahydro-$\beta$-carboline-1-carboxylic acid 3.03 g of 3-(2-aminoethyl)-4-ethoxycarbonylindole are picked up in 13 ml 1N hydrochloric acid and a little water. The clear filtered solution is added drop by drop while stirring to a solution of 1.25 g of gloyoxylic acid monohydrate in 40 ml of water cooled to 15° C. The reaction mixture is adjusted to pH 4 with sodium hydroxide solution. After having been left standing for one hour at 15° C., the precipitate is suctioned off. The filtrate is left standing overnight at room temperature. 800 mg of 5-ethoxycarbonyl-1,2,3,4-tetrahydro-$\beta$-carboline-1-carboxylic acid crystallize as yellow crystals with a 229°–231° C. melting point.

EXAMPLE 55

6,7-dimethoxy-4-ethyl-$\beta$-carboline 6,7-dimethoxy-4-ethyl-$\beta$-carboline with a 197° C. melting point is obtained according to the method in example 54. 6,7-dimethoxy-4-ethyl-1,2,3,4-tetrahydro-$\beta$-carboline-1-carboxylic acid required as starting material is obtained in the following manner:

(A) 1.3 g of isopropyl-[1-(5,6-dimethoxyindol-3-yl)-propyl]-amine and 1.3 ml of nitromethane in 50 ml of acetonitrile, after addition of 320 mg of n-tributylphosphine in 20 ml of acetonitrile, are refluxed for 3 hours under an $N_2$ atmosphere.

The reaction mixture is concentrated to dryness and picked up in methylene chloride. The organic phase is extracted with 0.5N hydrochloric acid, washed with saturated sodium chloride solution and the organic phase is dried on Sikkon. After distilling off of the solvent, the resulting raw product is chromatographed on silica gel (methylene chloride). 0.98 g of 2-(5,6-dimethoxyindol-3-yl)1-nitrobutane is obtained as an oil.

(B) 2-(5,6-dimethoxyindol-3-yl)-1-aminobutane 0.98 g of 2-(5,6-dimethoxyindol-3-yl)-1-nitrobutane is reduced in 20 ml of ethanol with 1 g of Raney nickel catalyst at room temperature under a hydrogen atmosphere of 50 bar. The catalyst is filtered off and the filtrate evaporated.

2-(5,6-dimethoxyindol-3-yl)-1-aminobutane is obtained in quantitative yield which is immediately further reacted according to example 54(C) to 6,7-dimethoxy-4-ethyl-1,2,3,4-tetrahydro-$\beta$-carboline-1-carboxylic acid.

EXAMPLE 56

5-benzyloxy-4-methoxymethyl-$\beta$-carboline 0.9 g of 5-benzyloxy-4-methoxymethyl-1,2,3,4-tetrahydro-$\beta$-carboline-1-carboxylic acid is suspended in 20 ml of xylene and refluxed for 1.5 hours. The solvent is distilled off under vacuum. The residue is picked up in 20 ml dimethylsulfoxide, mixed with 0.14 g of sulfur and stirred for 1 hour at 140° C. bath temperature. Dimethylsulfoxide is distilled off under vacuum. The resulting yellow oil is absorptively extracted with diisopropyl ether.

The crystalline residue is recrystallized from ethyl acetate. 0.320 g of 5-benzyloxy-4-methoxymethyl-$\beta$-carboline with a 189°–191° C. melting point is obtained.

The 5-benzyloxy-4-methoxymethyl-1,2,3,4-tetrahydro-$\beta$-carboline-1-carboxylic acid required as starting material is synthesized according to the method indicated in example 54.

EXAMPLE 57

5-acetyl-$\beta$-carboline 5-acetyl-1,2,3,4-tetrahydro-$\beta$-carboline is also dehydrogenated according to the method described in example 54 (production of $\beta$-carboline-5-carboxylic acid ethyl esters). The 5-acetyl-$\beta$-carboline is obtained in a 10% yield.

The 5-acetyl-1,2,3,4-tetrahydro-$\beta$-carboline required as starting material is produced starting from 4-acetylindole by the 4-acetyl-3-(2-nitrovinyl)-indole according to the method described in example 54 for production of 1,2,3,4-tetrahydro-$\beta$-carboline-5-carboxylic acid ethyl ester.

EXAMPLE 58

$\beta$-carboline-5-carboxylic acid nitrile $\beta$-carboline-5-carboxylic acid nitrile is produced, analogously to the process of R. S. Monson and D. N. Priest [Canad. J. Chem. 49, 2897 (1971)] by boiling of the amide in hexamethylphosphoric triamide.

The $\beta$-carboline-5-carboxylic acid amide required as starting material is obtained by reaction of $\beta$-carboline-5-carboxylic acid ethyl ester with saturated aqueous ammonia solution at 0° C.

EXAMPLE 59

$\beta$-carboline-5-carboxylic acid-butyl ester

The compound is produced from $\beta$-carboline-5-carboxylic acid ethyl ester by boiling in n-butanol with addition of a catalytic amount of p-toluenesulfonic acid.

EXAMPLE 60

$\beta$-carboline-3-phosphonic acid-diethyl ester

A mixture of 0.24 g of inole and 0.83 g of azadiene A (see below) is heated in 3.4 ml of acetic acid for 3 hours to 140° C. (bath temperature). When the solution is poured into ice water, 0.28 g of $\beta$-carboline-3-phosphonic acid-diethyl ester with a 196° C. melting point crystallizes.

EXAMPLE 61

5-benzyloxy-β-carboline-3-phosphonic acid-diethyl ester

Analogously to example 60, 0.50 g of the title compound with a 188° C. melting point (from diethyl ether/benzene) is obtained from 0.45 g of 4-benzylozyindole.

EXAMPLE 62

5-ethoxymethyl-β-carboline-3-phosphonic acid-diethyl ester

The title compound is obtained from 4-ethyoxymethylindole analogously to example 60.

EXAMPLE 63

β-carboline-3-phosphonic acid-monoethyl ester

Analogously to example 60, the monoester with >320° C. melting point (decomposition) is obtained in the presence of a catalytic amount of sulfuric acid.

EXAMPLE 64

β-carboline-3-phosphonic acid-monoethyl-monomethyl ester 0.28 g of the monoethyl ester of example 63 is dissolved in methanol and left standing overnight with excess ether diazomethane solution. 0.21 g of the title compound is obtained.

EXAMPLE 65

5-benzyloxy-β-carboline-3-phosphonic acid-monoethyl ester-diethylamide

A mixture of 0.2 g of 5-benzyloxy-β-carboline-3-phosphonic acid diethyl ester (example 61) and 0.1 g of oxalyl chloride in 10 ml of dichloromethane is stirred for 24 hours at room temperature and then mixed with an excess of diethylamine. It is heated to boiling for 2 more hours for completion of the reaction. It is diluted with acetic acid and extracted with water. The evaporation residue of the organic phase yields 0.15 g of the title compound after crystallization from tetrahydrofuran.

EXAMPLE 66

3-phenyl-β-carboline

Analogously to example 60, the title compound with a 228° C. melting point (from isopropanol) is obtained from indole and $N^2$-(2-dimethyl-amino-1-phenylvinyl)-$N^1,N^1$-dimethylformamidine (azadiene B).

EXAMPLE 67

5-methyl-β-carboline-3-sulfonic acid-dimethylamide

Analogously to example 60, the title compound is obtained from 4-methylindole and azadiene C.

Azadienes A–C used in examples 60–67 are produced in the following manner:

Azadiene A:
  2-dimethylamino-1-(dimethylaminomethyleneamino)-ethylene-phosphonic acid-diethyl ester
    A mixture of 3.7 g of aminomethanephosphonic acid-diethyl ester and 15 g of the aminal ester tert-butyoxy-N,N,N',N'-tetramethylmethanediamine is heated to about 160° C. for 6 hours. 4.2 g are obtained after fractionating of the residue in a bulb tube at 160°–165° C.

Azadiene B:
  $N^2$-(2-dimethylamino-1-phenylvinyl)-$N^1,N^1$-dimethylformamidine
    According to W. Kantlehner et al., Liebigs Ann. Chem. 1980, 344.

Azadiene C:
  2-dimethylamino-1-(dimethylaminomethyleneamino)-ethylene-sulfonic acid-dimethylamide
    Production takes places analogously to azadiene A from aminomethanesulfonic acid-dimethylamide and aminal ester.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A β-carboline of the formula

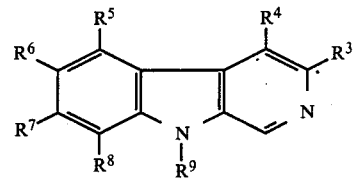

wherein
$R^3$ is halogen;
$OR^I$, wherein $R^I$ is H, $C_{1-5}$ alkyl, $C_{3-7}$-cycloalkyl, $C_{7-10}$-aralkyl or $C_{6-10}$-aryl;
$NR^{II}R^{III}$, wherein $R^{II}$ is H, $C_{1-5}$ alkyl, $C_{3-7}$-cycloalkyl, $C_{7-10}$-aralkyl or $C_{6-10}$-aryl and $R^{III}$ is $C_{1-5}$ alkyl, $C_{1-3}$-alkanoyl, $C_{1-6}$ alkoxycarbonyl, carbamoyl, or $R^{II}$ and $R^{III}$ together with the connecting N-atom are pyrrolyl or piperidino;
$SO_nR^I$, wherein n is 0, 1 or 2 and $R^I$ is as defined above;
$PO_3R^{IV}R^V$, wherein $R^{IV}$ and $R^V$ each independently is H, $C_{1-5}$-alkyl, $C_{3-7}$-cycloalkyl, $C_{7-10}$-aralkyl or $C_{6-10}$ aryl; or
$C_{3-7}$-cycloalkyl, $C_{8-12}$-aralkenyl, or $C_{6-10}$-aryl, each of whose alkyl portion is optionally substituted by 1 to 3 of halogen, $OR^I$, $NR^{II}R^{III}$, $SO_nR^I$, $COOR^I$, $CONR^{II}R^{III}$, $CSNR^{II}R^{III}$, $PO_3R^{IV}R^V$, $COR^I$ or CN, wherein $R^I$, $R^{II}$, $R^{III}$, $R^{IV}$, $R^V$ and n are as defined above;
$R^4$ is H, $C_{1-5}$ alkyl, $C_{1-5}$ alkoxy-$C_{1-5}$-alkyl, $COR^{VI}$ or $CSR^{VII}$, wherein $R^{VI}$ is H, $C_{1-5}$-alkyl, $C_{3-7}$-cycloalkyl, $C_{7-10}$-aralkyl, OH, O-$C_{1-5}$-alkyl, O-$C_{3-7}$-cycloalkyl, O-$C_{7-10}$-aralkyl or $NR^{II}R^{II}$, wherein $R_{II}$ is as defined above and the $R^{II}$'s can be the same or different or both $R^{II}$'s together with the N are pyrrolyl or piperidino and wherein $R^{VII}$ is H, $C_{1-5}$ alkyl, $C_{3-7}$-cycloalkyl or $C_{7-10}$-aralkyl;
$R^5$-$R^8$ each independently is H, halogen, $NO_2$, $OR^I$, $NR^{II}R_{III}$, $PO_3R^{IV}R^V$, $SO_2NR^IR^V$, $COOR^I$, $CONR^{II}R^{III}$, $CSNR^{II}R^{III}$ and $COR^I$ wherein $R^{I-V}$ are as defined above and at most two of $R^5$-$R^8$ can be non-H; and $R^9$ is H, $C_{1-5}$ alkyl, $C_{1-3}$-alkanoyl, carbamoyl, $C_{1-6}$-alkoxycarbonyl, or $SO_2R^{VIII}$ wherein $R^{VIII}$ is methyl or p-tolyl.

2. 6-bromo-O-(tetrahydropyran-2-yl)-β-carboline-3-methanol
   6-bromo-9-tosyl-O-(tetrahydropyran-2-yl)--carboline-3-methanol
   N-phenyl-carbamic acid-(β-carboline-3-yl-methyl)-ester
   3-chloromethyl-β-carboline
   3-(1-chloroethyl)-β-carboline
   3-styryl-β-carboline
   3-methylthiomethyl-β-carboline
   3-methylsulfinylmethyl-β-carboline
   3-methylsulfonylmethyl-β-carboline, or
   3-diethylphosphonomethyl-βcarboline,
   each a compound of claim 1.

3. 6-iodo-3-methylsulfinyl-β-carboline
   6-benzyloxycarbonyl-3-methylsulfinyl-β-carbonyl
   6-ethoxycarbonyl-3-methylsulfinyl-β-carboline, or,
   each a compound of claim 1.

4. 3-tert-butoxycarbonylamino-β-carboline
   3-methoxycarbonylamino-β-carboline
   3-acetamino-β-carboline
   3-(1-pyrrolyl)-β-carboline, or
   3-piperidino-β-carboline,
   each a compound of claim 1.

5. 3-ethoxy-β-carboline
   3-methoxy-β-carboline
   3-propoxy-β-carboline
   3-isopropoxy-β-carboline
   3-benzyloxy-β-carboline
   3-cyclohexyloxy-β-carboline
   3-(1-methoxyethoxy)-β-carboline
   3-tert-butoxy-β-carboline
   3-butoxy-β-carboline
   3-isopentoxy-β-carboline
   3-ethylthio-β-carboline
   4-methyl-3-methylthio-β-carboline
   3-benzylthio-β-carboline
   3-methylthio-β-carboline
   6-nitro-3-methylthio-β-carboline
   6-amino-3-methylthio-β-carboline, or
   6-diallylamino-3-methylthio-β-carboline,
   each a compound of claim 1.

6. 6-chlorosulfonyl-3-methylthio-β-carboline
   6,8-bis(chlorosulfonyl)-3-methylthio-β-carboline
   6-dimethylaminosulfonyl-3-methylthio-β-carboline
   6,8-bis(dimethylaminosulfonyl)-3-methylthio-β-carboline
   6-diallylaminosulfonyl-3-methylthio-β-carboline, or
   6,8-bis(diallylaminosulfonyl)-3-methylthio-β-carboline,
   each a compound of claim 1.

7. β-carboline-3-phosphonic acid-diethyl ester
   5-benzyloxy-β-carboline-3-phosphonic acid-diethyl ester
   5-ethoxymethyl-β-carboline-3-phosphonic acid-diethyl ester
   β-carboline-3-phosphonic acid-monoethyl ester
   β-carboline-3-phosphonic acid-monoethyl-monomethyl ester
   5-benzyloxy-β-carboline-3-phosphonic acid-monoethyl ester-diethylamide
   3-phenyl-β-carboline, or
   5-methyl-β-carboline-3-sulfonic acid-dimethylamide,
   each a compound of claim 1.

8. N-methyl-carbamic acid-(9-methyl-carbamoyl-β-carboline-3-yl-methyl)ester,
   3-(1-ethyl-1-hydroxy-propyl)-β-carboline or,
   3-(1-hydroxyethyl)-β-carboline,
   each a compound of claim 1.

9. 3-hydroxy-β-carboline,
   3-bromo-β-carboline,
   3-chloro-β-carboline,
   each a compound of claim 1.

10. A β-carboline of the formula wherein
$R^3$ is $OR^I$, wherein $R^I$ is $C_{1-5}$-alkyl, $C_{3-7}$-cycloalkyl or $C_{7-10}$-aralkyl;
$NR^{II}R^{III}$, wherein $R^{II}$ is H and $R^{III}$ is $C_{1-3}$-acyl or $C_{1-6}$-alkoxycarbonyl, or $R^{II}$ and $R^{III}$ together with the connecting N-atom are pyrrolyl or piperidino; or
$SC_{1-5}$-alkyl or $SC_{7-10}$-arylalkyl;
$R^4$ is H, $C_{1-5}$-alkyl or $C_{1-5}$-alkoxy-$C_{1-5}$-alkyl;
$R^6$ and $R^8$ each independently is H, $SO_2Cl$, $NO_2$, $NR^{IV}_2$ or $SO_2NR^{IV}_2$ wherein $R^{IV}$ is H, $C_{1-5}$-alkyl or allyl; and
$R^5$, $R^7$ and $R^9$ are H.

11. A compound of claim 10, wherein $R^6$ and $R^8$ are each independently H, $NO_2$, $NH_2$, $N(C_{1-5}$-alkyl$)_2$, $SO_2NH_2$ or $SO_2N$-$(C_{1-5}$-alkyl$)_2$.

12. A compound of claim 1 wherein $R^3$ is $OR^I$.

13. A compound of claim 1 wherein $R^3$ is $SR^I$.

14. A compound of claim 12 wherein $R^I$ is $C_{1-5}$-alkyl, $C_{7-10}$-aralkyl or $C_{6-10}$ aryl.

15. A compound of claim 13 wherein $R^I$ is $C_{1-5}$-alkyl or $C_{7-10}$ aralkyl.

16. A compound of claim 14 wherein $R^4$ is H, $C_{1-5}$-alkyl or $C_{1-5}$-alkoxy-$C_{1-5}$-alkyl.

17. A compound of claim 15 wherein $R^4$ is H, $C_{1-5}$-alkyl or $C_{1-5}$-alkoxy-$C_{1-5}$-alkyl.

18. A compound of claim 16 wherein $R^6$ is H, $NO_2$, $NR^aR^b$ or $SO_2NR^aR^b$, and $R^a$ and $R^b$ are the same or different and each is H or $C_{1-5}$-alkyl.

19. A pharmaceutical composition comprising a tranquilizing effective amount of a compound of the formula wherein
$R^3$ is halogen;
$OR^I$, wherein $R^I$ is H, $C_{1-5}$ alkyl, $C_{3-7}$-cycloalkyl, $C_{7-10}$-aralkyl or $C_{6-10}$-aryl;
$NR^{II}R^{III}$, wherein $R^{II}$ is H, $C_{1-5}$ alkyl, $C_{3-7}$-cycloalkyl, $C_{7-10}$-aralkyl or $C_{6-10}$-aryl and $R^{III}$ is $C_{1-5}$ alkyl, $C_{1-3}$-alkanoyl, $C_{1-6}$alkoxycarbonyl, carbamoyl, or $R^{II}$ and $R^{III}$ together with the connecting N-atom are pyrrolyl or piperidino;

$SO_nR^I$, wherein n is 0, 1 or 2 and $R^I$ is as defined above;

$PO_3R^{IV}R^V$, wherein $R^{IV}$ and $R^V$ each independently is H, $C_{1-5}$-alkyl, $C_{3-7}$-cycloalkyl, $C_{7-10}$-aralkyl or $C_{6-10}$ aryl; or $C_{3-7}$-cycloalkyl, $C_{8-12}$-aralkenyl, or $C_{6-10}$-aryl, each of whose alkyl portion is optionally substituted by 1 to 3 of halogen, $OR^I$, $NR^{II}R^{III}$, $SO_nR^I$, $COOR^I$, $CONR^{II}R^{III}$, $CSNR^{II}R^{III}$, $PO_3R^{IV}R^V$, $COR^I$ or CN, wherein $R^I$, $R^{II}$, $R^{III}$, $R^{IV}$, $R^V$ and n are as defined above;

$R^4$ is H, $C_{1-5}$ alkyl, $C_{1-5}$ alkoxy-$C_{1-5}$-alkyl, $COR^{VI}$ or $CSR^{VII}$, wherein $R^{VI}$ is H, $C_{1-5}$-alkyl-$C_{3-7}$-cycloalkyl, $C_{7-10}$-aralkyl, OH, O-$C_{1-5}$-alkyl, O-$C_{3-7}$-cycloalkyl, O-$C_{7-10}$-aralkyl or $NR^{II}R^{II}$, wherein $R_{II}$ is as defind above and the $R^{II}$'s can be the same or different or both $R^{II}$'s together with the N are pyrrolyl or piperidino and wherein $R^{VII}$ is H, $C_{1-5}$ alkyl, $C_{3-7}$-cycloalkyl or $C_{7-10}$-aralkyl;

$R^5$-$R^8$ each independently is H, halogen, $NO_2$, $OR^I$, $NR^{II}R^{III}$, $PO_3R^{IV}R^V$, $SO_2NR^IR^V$, $COOR^I$, $CONR^{II}R^{III}$, $CSNR^{II}R^{III}$ and $COR^I$ wherein $R^{I-V}$ are as defined above and at most two of $R^5$-$R^8$ can be non-H; and $R^9$ is H, $C_{1-5}$ alkyl, $C_{1-3}$-alkanoyl, carbamoyl, $C_{1-6}$-alkoxycarbonyl, or $SO_2R^{VIII}$ wherein $R^{VIII}$ is methyl or p-tolyl, and a pharmaceutically acceptable carrier.

20. A method of achieving a tranquilizing effect in a patient in need of such treatment comprising administering to the patient a tranquilizng effective amount of a compound of the formula

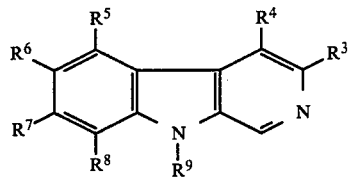

wherein $R^3$ is halogen;

$OR^I$, wherein $R^I$ is H, $C_{1-5}$alkyl, $C_{3-7}$-cycloalkyl, $C_{7-10}$-aralkyl or $C_{6-10}$-aryl;

$NR^{II}R^{III}$, wherein $R^{II}$ is H, $C_{1-5}$ alkyl, $C_{3-7}$-cycloalkyl, $C_{7-10}$-aralkyl or $C_{6-10}$-aryl and $R^{III}$ is $C_{1-5}$ alkyl, $C_{1-3}$-alkanoyl, $C_{1-6}$ alkoxycarbonyl, carbamoyl, or $R^{II}$ and $R^{III}$ together with the connecting N-atom are pyrrolyl or piperidino;

$SO_nR^I$, wherein n is 0, 1 or 2 and $R^I$ is as defined above;

$PO_3R^{IV}R^V$, wherein $R^{IV}$ and $R^V$ each independently is H, $C_{1-5}$-alkyl, $C_{3-7}$-cycloalkyl, $C_{7-10}$-aralkyl or $C_{6-10}$ aryl; or $C_{3-7}$-cycloalkyl, $C_{8-12}$-aralkenyl, or $C_{6-10}$-aryl, each of whose alkyl portion is optionally substituted by 1 to 3 of halogen, $OR^I$, $NR^{II}R^{III}$, $SO_nR^I$, $COOR^I$, $CONR^{II}R^{III}$, $CSNR^{II}R^{III}$, $PO_3R^{IV}R^V$, $COR^I$ or CN, wherein $R^I$, $R^{II}$, $R^{III}$, $R^{IV}$, $R^V$ and n are as defined above;

$R^4$ is H, $C_{1-5}$ alkyl, $C_{1-5}$ alkoxy-$C_{1-5}$-alkyl, $COR^{VI}$ or $CSR^{VII}$, wherein $R^{VI}$ is H, $C_{1-5}$-alkyl, $C_{3-7}$-cycloalkyl, $C_{7-10}$-aralkyl, OH, O-$C_{1-5}$-alkyl, O-$C_{3-7}$-cycloalkyl, O-$C_{7-10}$-aralkyl or $NR^{II}R^{II}$, wherein $R_{II}$ is as defined above and the $R^{II}$'s can be the same or different or both $R^{II}$'s together with the N are pyrrolyl or piperidino and wherein $R^{VII}$ is H, $C_{1-5}$ alkyl, $C_{3-7}$-cycloalkyl or $C_{7-10}$-aralkyl;

$R^5$-$R^8$ each independently is H, halogen, $NO_2$, $OR^I$, $NR^{II}R^{III}$, $PO_3R^{IV}R^V$, $SO_2NR^IR^V$, $COOR^I$, $CONR^{II}R^{III}$, $CSNR^{II}R^{III}$ and $COR^I$ wherein $R^{I-V}$ are as defined above and at most two of $R^5$-$R^8$ can be non-H; and $R^9$ is H, $C_{1-5}$ alkyl, $C_{1-3}$-alkanoyl, carbamoyl, $C_{1-6}$-alkoxycarbonyl, or $SO_2R^{VIII}$ wherein $R^{VIII}$ is methyl or p-tolyl.

21. A composition of claim 1, wherein when $R^3$ is pyrrolyl or piperidino.

22. A pharmaceutical composition comprising a tranquilizing effective amount of a compound of claim 10.

23. A method of achieving a tranquilizing effect in a patient in need of such treatment comprising administering to the patient a tranquilizing effective amount of a compound of claim 10.

* * * * *